United States Patent [19]
Tomaszewski et al.

[11] Patent Number: 5,348,534
[45] Date of Patent: Sep. 20, 1994

[54] TAMPON APPLICATOR

[75] Inventors: Gina M. Tomaszewski, Monson; Garrett Cavanaugh, Three Rivers, both of Mass.

[73] Assignee: Tambrands Inc., White Plains, N.Y.

[21] Appl. No.: 973,156

[22] Filed: Nov. 6, 1992

[51] Int. Cl.$^5$ .............................. A61F 13/20
[52] U.S. Cl. ...................... 604/14; 604/11; 604/13; 604/904
[58] Field of Search .................. 604/11–18, 604/904

[56] References Cited

U.S. PATENT DOCUMENTS

| | | |
|---|---|---|
| 3,204,635 | 9/1965 | Voss et al. |
| 3,347,234 | 10/1967 | Voss. |
| 4,453,925 | 6/1984 | Decker ........................... 604/14 |
| 4,508,531 | 4/1985 | Whitehead ..................... 604/14 |
| 5,087,239 | 2/1992 | Beastall et al. ................. 604/14 |

FOREIGN PATENT DOCUMENTS

| | | |
|---|---|---|
| 2314819 | 10/1973 | Fed. Rep. of Germany. |
| 2114448A | 8/1983 | United Kingdom. |
| 2132484A | 7/1984 | United Kingdom. |
| 2142906 | 1/1985 | United Kingdom. |

*Primary Examiner*—Randall L. Green
*Assistant Examiner*—P. Zuttarelli
*Attorney, Agent, or Firm*—Fish & Richardson

[57] ABSTRACT

An improved tampon applicator for insertion of a tampon into a body cavity is provided, including a paper tampon holder tube having an expulsion end dimensioned for insertion into the body cavity and including a plurality of contiguous segments separated by slits, and a plunger, telescopically and slidably mounted in the holder distal to the expulsion end and adapted to expel the tampon from the holder when pushed manually into the holder. As the tampon is expelled, the segments bend open at a hinge region. The segments of the improved applicator bend outwardly during expulsion with significantly reduced applied force, improving user comfort. In one aspect, the tampon holder includes a plurality of small cuts extending circumferentially from the slits through the paper in the vicinity of the hinge region. The cuts reduce the width of the petal segments, and thereby reduce the bending moment and rigidity at the hinge region. In another aspect, the tampon holder includes a zone of indentation, preferably a plurality of score lines, disposed on the inside of the tampon holder tube in the vicinity of the hinge region.

17 Claims, 3 Drawing Sheets

TAMPON APPLICATOR

BACKGROUND OF THE INVENTION

This invention relates to a tampon applicator, formed from a paper laminate.

Tampon applicators comprising a pair of telescopically arranged tubes have long been known in the art. Typically, these applicators comprise a tampon holder tube and a plunger tube, telescopically disposed such that a portion of the plunger tube is within the holder tube.

Some applicators have the tampon exposed at the end intended for vaginal insertion (the expulsion end), while others provide a rounded expulsion end, with the tampon covered by a plurality of segments, referred to in the art as "petals", which open during tampon expulsion. A tampon having the latter construction is disclosed in U.S. Pat. No. 5,087,239, the disclosure of which is incorporated herein by reference. In this applicator, a weakened region, e.g., a groove, is provided at the base of the segments. The weakened region functions as a hinge, reducing the force required to bend the segments outwardly during expulsion.

However, the force required to bend the segments during expulsion may be undesirably high, even if a groove is provided at the base of the segments. This occurs particularly when a thick, stiff paper laminate, or a laminate including a layer of cellophane or polymeric film, as disclosed in copending application U.S. Ser. No. 07/819,753, is used in a segment construction. The high force required may cause discomfort to the user, or may prevent the tampon from being properly expelled.

SUMMARY OF THE INVENTION

The invention features an improved tampon applicator for insertion of a tampon into a body cavity, including a paper tampon holder tube having an expulsion end dimensioned for insertion into the body cavity and including a plurality of contiguous petal segments separated by slits, and a plunger, telescopically and slidably mounted in the holder distal to the expulsion end and adapted to expel the tampon from the holder when pushed manually into the holder. As the tampon is expelled, the segments bend open at a hinge region. The segments of the improved applicator bend outwardly during expulsion with significantly reduced applied force, improving user comfort.

In one aspect, the tampon holder includes a plurality of small cuts extending circumferentially from the petal slits in the vicinity of the hinge region. The cuts may take a variety of forms, so long as they narrow the circumferential extent, i.e., the width, of the petal segments. The cuts reduce the bending moment and rigidity at the hinge region, both by shortening the width of the "beam" being bent, and by reducing the curvature of the "beam". In preferred embodiments, the tampon holder is a paper laminate; there is a cut at or near the base of each petal slit; the cuts have a length that effectively narrows the width of the petal segments by anywhere from about 15 to 50 percent.

In another aspect, the tampon holder includes a zone of indentation disposed on the inside of the tampon holder tube in the vicinity of the hinge region. The zone may comprise a plurality of score lines, arranged in a variety of patterns, and the score lines may be continuous or discontinuous. In preferred embodiments, the tampon holder is a paper laminate; the score lines are combined with the circumferential cuts, both located in the vicinity of the hinge region so as to reduce the force required to bend the segments at the hinge region; the score lines extend circumferentially, and one or more of the score lines are disposed slightly above (closer to the distal end of the holder tube), and one or more slightly below the weakened region. Preferably, the depth of the score lines is from about 25 to 80 percent of the total thickness of the paper laminate.

Preferably, one or both of the circumferential cuts and interior score lines is combined with a further weakened region at the vicinity of the hinge region (e.g., a groove or scoring, which may be continuous or discontinuous), as shown in U.S. Pat. No. 5,087,239.

For particularly thick or stiff paper laminates, it may be desirable to use both circumferential cuts and interior score lines in combination. For thinner paper laminates, the circumferential cuts or the score lines may be used alone, as the combination of cuts and score lines may in some instances cause the segments to rip off.

Other features and advantages of the invention will be apparent from the following description of preferred embodiments, and from the claims.

DESCRIPTION OF THE PREFERRED EMBODIMENTS

Figure 1:
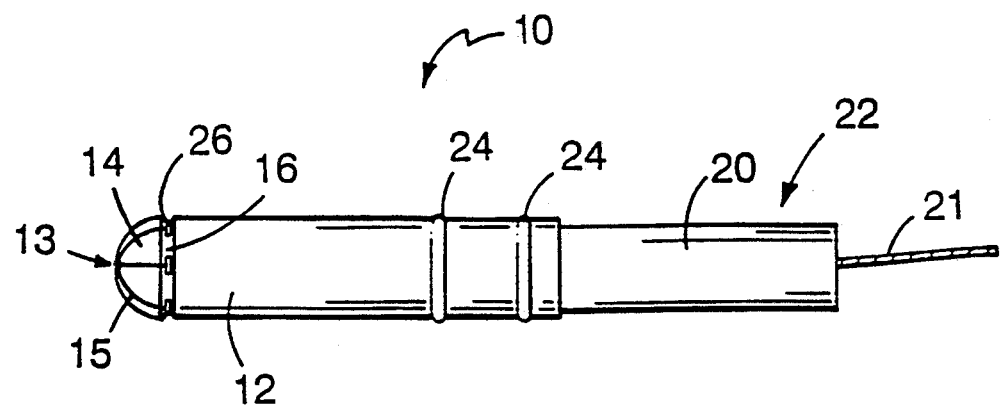
FIG. 1 shows a tampon applicator according to one embodiment of the invention.
Figure 2:
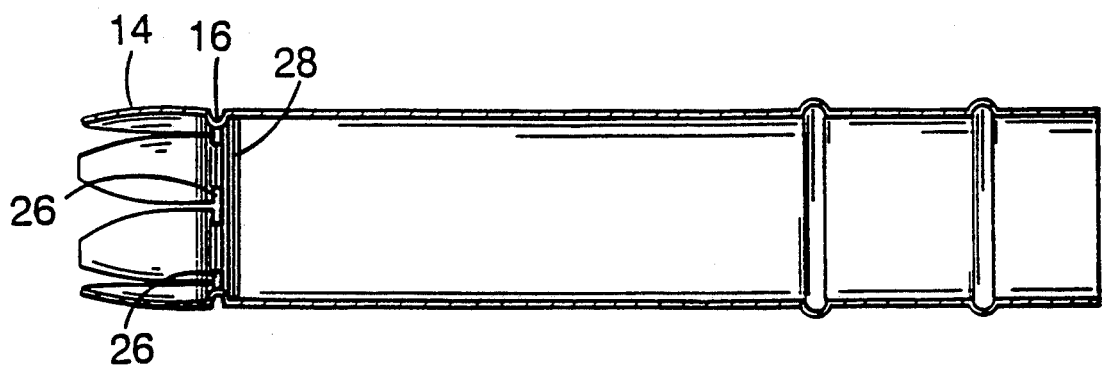
FIG. 2 shows a partial side cross-sectional view of the applicator of FIG. 1, enlarged to show detail.
Figure 2A:
FIG. 2a shows a front view of the triangular notches which are removed from the tampon expulsion end to form the petal segments.

An applicator 10 according to a preferred embodiment of the invention is shown in FIGS. 1 and 2. The applicator comprises tubular tampon holder 12, and plunger 20, telescopically and slidably mounted inside of tampon holder 12. A tampon 13 is retained within tampon holder 12, and its expulsion end is surrounded by contiguous petal segments 14, separated by petal slits 15. Petal segments 14 are formed by cutting out triangular notches of the paper laminate (as is known, e.g., in U.S. Pat. No. 5,087,239). This may occur either prior to formation of the tube by stamping, in convolutely wound tampons, or after formation of a spirally wound tube. The segments are then heat-formed into a dome-shape.

In use, as plunger 20 is pressed inwardly, petal segments 14 bend open at a hinge region, and the tampon is expelled through the expulsion end.

To reduce the expulsion force required to bend the petal segments open at the hinge region, a weakened region in the form of a groove 16 is embossed into the outer surface of tampon holder 12 in the vicinity of the hinge region. Groove 16 extends circumferentially around, at, or near, the base of the segments. The weakened region may take a variety of forms other than a groove (e.g., it may be a slot or perforation, and it may be continuous or discontinuous). Tampon withdrawal cord 21 extends out of distal end 22 of the applicator.

Rings 24 are embossed into tampon holder 12 at its distal end, to provide a gripping surface for the user.

Substantial further reduction in expulsion force is achieved by providing a plurality of small circumferential cuts 26 at the vicinity of the hinge region. Each cut extends circumferentially a small distance in each direction from the slit 15. The cuts reduce the bending moment and rigidity at the hinge region, both by shortening the width of the "beam" being bent, and by reducing the curvature of the "beam". In a preferred embodiment, each cut is from about 0.04 to 0.09" long, about 0.01 to 0.03" high, and has a width approximately equal to that of slits 15.

Further reduction in expulsion force is achieved by providing a zone of indentation, preferably a plurality of score lines 28, disposed on the inside of the tampon holder in the vicinity of the hinge region (FIG. 2). Score lines 28 are provided across an area extending from slightly above to slightly below groove 16, and are spaced about 0.030" apart. In alternate embodiments, the zone of indentation could be an embossed band in which the thickness of the holder is reduced; the depth of the embossing could be uniform or varying. If the zone is made up of score lines, there may be more score lines than shown in FIG. 2 (e.g., the score lines may extend further up the segments), or fewer score lines (e.g., only one on either side of the groove), and the score lines may be spaced closer or further apart, preferably from about 0.010 to 0.050" apart. Preferably, the depth of indentation in the zone is from about 25 to 80 percent of the total thickness of the paper laminate. For the preferred laminate, the score lines are about 0.008 to 0.010" deep. The score lines may be arranged in many other patterns, e.g., cross-hatching in which score lines intersect, and the scoring can be either continuous or discontinuous provided there is scoring around substantially the entire inner surface of the tampon holder. The score lines may be formed by any suitable process, but are typically formed by a mandrel and rolling die process. The circumferential cuts and score lines may be used in combination (as shown in FIG. 2) or alone, depending on the stiffness of the paper and desired expulsion pressure.

A preferred tampon holder 12 is constructed from a laminate of the following layers: three bleached Kraft outer paper layers and a cellophane layer disposed on the outer tube surface. It is preferred that both the tampon holder and the plunger have this construction, although the holder and the plunger may be made from different materials, e.g., plastic or wax-coated paper, or with ground-wood paper in some of the layers, if desired.

Each of the layers is adhered to adjoining layers by adhesive, preferably a water-based adhesive, to allow the layers to delaminate when the applicator is exposed to water, thereby permitting the applicator to be disposed of by flushing. The water-based adhesive also preserves the biodegradability of the product. Suitable adhesives include, for example, Dextrin TM (vegetable-based adhesive) and polyvinyl acetate, with polyvinyl acetate being preferred for its ability to bond to cellophane under humid storage conditions. Suitable polyvinyl acetate adhesives are commercially available from Findley Adhesives, Wauwatosa, Wis.

The cellophane layer may be of any grade of cellophane so long as it has adequate water resistance to maintain its integrity and remain tack-free when used in the invention, i.e. adequate to withstand humid environments for long periods of time, and to withstand insertion into the vagina, without becoming tacky or dissolving. Accordingly, the term does not refer to pure regenerated cellulose which is free from any additives or coatings, for such material has extremely low water resistance. Suitable cellophanes may contain additives or surface coatings which impart water resistance, with surface coatings being preferred. Preferred water resistant coatings are selected from the group consisting of nitrocellulose and polyvinylidene chloride, with nitrocellulose preferred for its biodegradability. A nitrocellulose coated cellophane sheet is commercially available from Flexel, Inc., Atlanta, Ga. Water resistance is typically measured in terms of Water Vapor Transmission Rate (WVTR). It is preferred that the cellophane film have a WVTR of less than about 100 $g/m^2/day$. It is preferred that the cellophane layer be thin relative to the paper layer. Preferably the thickness is less than about 0.0020 inches, more preferably less than 0.0009 inches.

It is preferred, for aesthetic reasons, that the outer paper layer be a white paper. Although any conventional paper may be used, it is preferred that the paper be selected from the group consisting of bleached Kraft paper and bleached sulfite paper. If no other paper layer is to be utilized, the white paper will be selected to have adequate rigidity to provide structural strength to the finished tube for its use as a tampon applicator. The paper may contain additional optical brighteners, e.g., stilbene derivatives, and the like to enhance the aesthetic appearance of the laminate. The brighteners, and overall whiteness of the paper, work in conjunction with the gloss of the cellophane layer to greatly improve the aesthetic appearance of the resulting applicator. Preferred thicknesses for the outer paper layer are in the range of 0.0015 to 0.005 inches, more preferably 0.003 inches.

Other polymers may be used in place of cellophane, although with loss of some of the unique advantages of cellophane for this application. A variety of thermoplastic polymers may be used. The polymers should be capable of being formed into a relatively thin sheet, and be themselves water-resistant or have a coating or additive which imparts water-resistance. Preferred polymers include but are not limited to cellophane, polyethylene, polyester, polypropylene, polycaprolactone, and ethylene vinyl acetate.

The tampon holder may have no outer cellophane or polymer layer, provided it has adequate rigidity to withstand the knurling and/or circumferential-cut operations. Suitable laminates which do not have a cellophane or polymer layer should be at least about 0.010 inch thick, preferably 0.010 to 0.020 inch thick.

Any conventional process can be used to form the tube, e.g., spiral or convolute winding of the individual layers, each layer on top of the previous layer about a common central axis. Spiral winding is generally preferred. It is also preferred that the seams formed in each layer during spiral winding be offset from the seams in other layers. These methods are well known to those skilled in the art.

Figure 3:
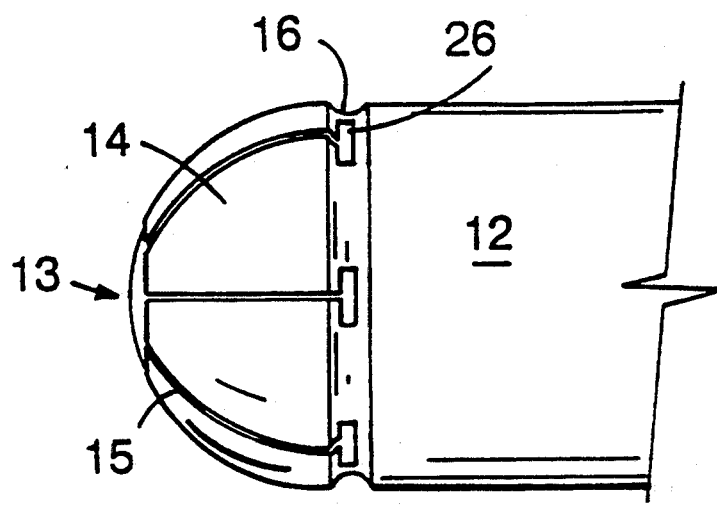
FIG. 3 is an enlarged view of the expulsion end of the embodiment shown in FIG. 1.
Figure 3A:
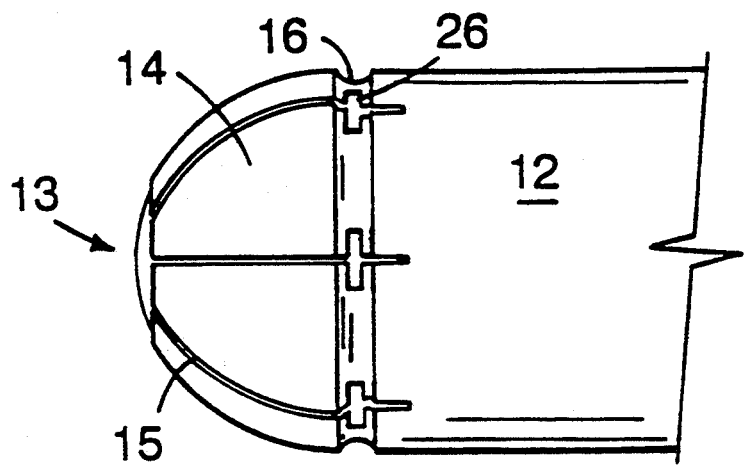
FIGS. 3a–3e show the expulsion ends of tampon applicators according to some of many alternate embodiments of the invention.
Figure 3B:
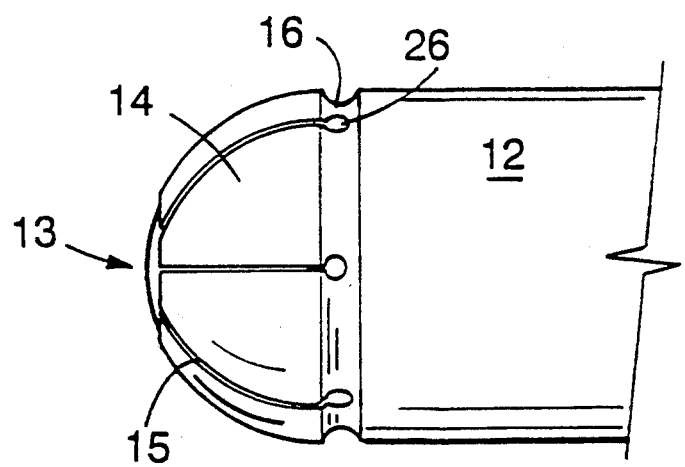
Figure 3C:
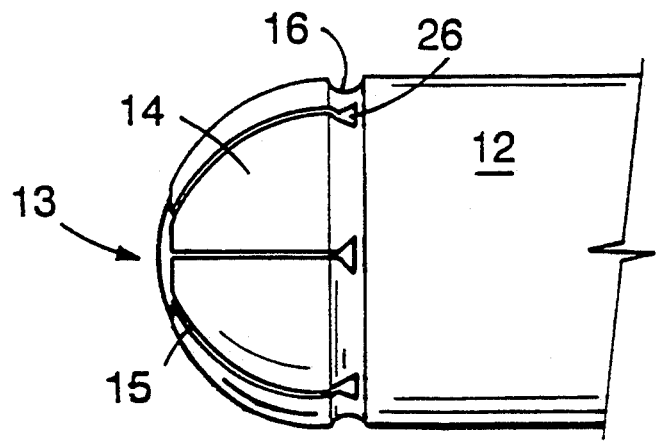
Figure 3D:
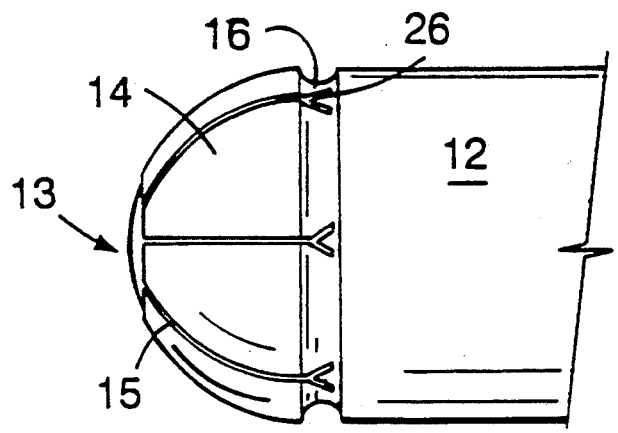
Figure 3E:
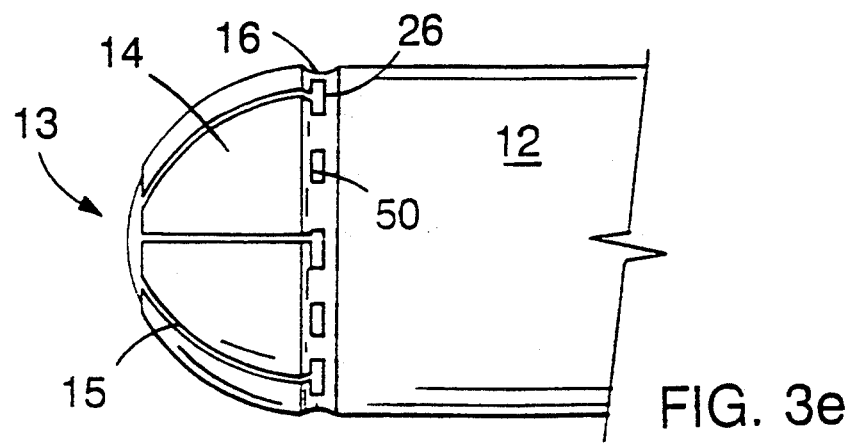

While preferred embodiments have been described above, other variations and modifications are within the scope of the following claims. As examples of the many possible variations, either the circumferential cuts or the score lines could be used by themselves, with or without groove 16 (or some other weakened region). The slits separating the petal segments can extend beyond the hinge region (e.g., as shown in FIG. 3a). The circumferential cuts and score lines need not be precisely aligned with one another, nor with groove 16 (or other weakened region), although typically expulsion force is minimized if the features are aligned. The circumferential cuts need not extend exactly circumferentially, but could be cut at an angle to the circumferential direction (as shown in FIG. 3d); and other shapes such as circular and triangular cut outs (as shown in FIGS. 3b and 3c) could be used, as long as they have some circumferential extent. The cuts need not actually remove material, as shown, but could simply be slits in the paper. The cuts need not be centered on the slits (as shown in FIGS. 3 and 3a), but could be offset (as shown in FIG. 3e), and the alignment with slits could vary randomly from slit to slit (FIG. 3e). Additional cuts could be positioned intermediate the slits (as at 50 in FIG. 3e). Although a laminated paper construction has been disclosed, the invention could be applied to nonlaminated paper constructions, and to plastic applicators.

We claim:

1. A tampon applicator for insertion of a tampon into a body cavity, comprising
    a tampon holder tube having a longitudinal axis and an expulsion end dimensioned for insertion into the body cavity, said tampon holder tube including interior and exterior surfaces.
    a plurality of segments integral with and extending from the expulsion end, each segment having a width and thickness, with slits separating the segments, and
    a circumferentially-extending weakening formation on the exterior of the holder tube, the formation defining a circumferential hinge at which said segments bend open during expulsion;
    a plunger, telescopically and slidably mounted in said holder and adapted to expel said tampon from said holder when pushed manually into said holder;
    said tampon holder tube further including
        a plurality of circumferentially-extending score lines, defining a zone of indentation extending along said longitudinal axis, the score lines being disposed on the inside surface of the tampon holder tube and the zone axially overlapping the weakening formation on the exterior surface of the holder tube, thereby weakening the holder tube at the circumferential hinge and reducing the force required to push the plunger into the holder to expel the tampon.

2. The applicator of claim 1 wherein said tampon holder tube comprises at least one layer of paper.

3. The applicator of claim 2 wherein said weakening formation comprises a circumferential groove.

4. The applicator of claim 2 wherein said circumferentially extending weakened formation comprises a circumferential groove and wherein said zone of indentation extends distance in each direction longitudinally from said groove.

5. The applicator of claim 2 wherein the tampon holder tube comprises a paper laminate and the depth of the score lines is from about 25 to 80 percent of the total thickness of the paper laminate.

6. The applicator of claim 2 wherein said paper is laminated and comprises an outer paper layer and a cellophane layer adhered to said paper layer on its outer surface, said cellophane layer having adequate water resistance to maintain its integrity during insertion into the body cavity.

7. An applicator of claim 6 wherein said laminate further comprises at least one inner paper layer, disposed adjacent the inner surface of said outer paper layer.

8. The applicator of claim 2 wherein said tampon holder tube includes a plurality of circumferentially-extending cuts, each cut being located adjacent said hinge and extending entirely through the thickness of a segment, and circumferentially from a slit a distance sufficient to narrow the width of the segment, thereby weakening the holder tube at the circumferential hinge and further reducing the force required to push the plunger into the holder to expel the tampon.

9. The applicator of claim 8 wherein said weakening formation comprises a circumferential groove and said cuts extend in said circumferential groove.

10. The applicator of claim 8 wherein said circumferential cuts extend from the ends of the slits separating the segments.

11. The applicator of claim 8 wherein at each slit there is only one circumferential cut, which extends circumferentially a small distance in one direction from said slit.

12. The applicator of claim 8 wherein at each slit there are two circumferential cuts, one extending circumferentially a small distance in each circumferential direction.

13. The applicator of claim 8 wherein said circumferential cuts include cuts having both a circumferential and a longitudinal extent.

14. The applicator of claim 2 wherein said circumferential cuts reduce the width of the petal segments from about 15 to 50 percent.

15. An applicator of claim 1, 2 or 8 wherein said tampon holder tube has a dome-shaped expulsion end.

16. A tampon applicator for insertion of a tampon into a body cavity, comprising
    a tampon holder tube having a longitudinal axis and an expulsion end dimensioned for insertion into the body cavity, the tampon holder tube including interior and exterior surfaces,
    a plurality of segments integral with and extending from the expulsion end, each segment having a width and thickness, with slits separating the segments, and
    a circumferentially extending weakening formation on the exterior of the holder tube, the formation defining a circumferential hinge at which said segments bend open during expulsion, and
    a plunger, telescopically and slidably mounted in said holder distal to said expulsion end and adapted to expel said tampon from said holder when pushed manually into said holder;
    said tampon holder further including a plurality of circumferentially-extending score lines, defining a zone of indentation extending along said longitudinal axis, the score lines being disposed on the inside surface of the tampon holder tube, and the zone axially overlapping the weakening formation on the exterior surface of the holder tube, and a plurality of cuts, each cut being located adjacent the hinge and extending entirely through the thickness of a segment, and circumferentially from a slit a distance sufficient to narrow the width of the segment, said cuts and said score lines thereby weakening the holder tube at the circumferential hinge and reducing the force required to push the plunger into the holder to expel the tampon.

17. A tampon applicator for insertion of a tampon into a body cavity, comprising a tampon holder tube having a longitudinal axis and an expulsion end dimensioned for insertion into the body cavity, the tampon holder tube including interior and exterior surfaces, a plurality of segments integral with and extending from the expulsion end, each segment having a width and thickness, with slits separating the segments, and a circumferentially extending weakening formation on the exterior of the holder tube, the formation defining a circumferential hinge at which said segments bend open during expulsion, and a plunger, telescopically and slidably mounted in said holder distal to said expulsion end and adapted to expel said tampon from said holder when pushed manually into said holder;

said tampon holder further including a plurality of circumferentially-extending score lines, defining a zone of indentation extending along said longitudinal axis, the score lines being disposed on the inside surface of the tampon holder tube, and the zone axially overlapping the weakening formation on the exterior surface of the holder tube, and a plurality of cuts, each cut being located adjacent the hinge and extending entirely through the thickness of a segment, and circumferentially from a slit a distance sufficient to narrow the width of the segment, at least one of said cuts having both a circumferential and a longitudinal extent, said cuts and said score lines thereby weakening the holder tube at the circumferential hinge and reducing the force required to push the plunger into the holder to expel the tampon.

* * * * *